United States Patent [19]

Shuto et al.

[11] Patent Number: 5,972,949
[45] Date of Patent: Oct. 26, 1999

[54] ETHER COMPOUNDS AND THEIR USE

[75] Inventors: Akira Shuto, Ashiya; Hirosi Kisida; Toru Tsuchiya, both of Takarazuka; Yoji Takada, Toyonaka; Hiroaki Fujimoto, Funabashhi, all of Japan

[73] Assignee: Sumito Chemical Co., Ltd., Osaka-fu, Japan

[21] Appl. No.: 09/174,010

[22] Filed: Oct. 16, 1998

Related U.S. Application Data

[62] Division of application No. 08/727,565, Dec. 6, 1996, Pat. No. 5,883,262.

[30] Foreign Application Priority Data

Apr. 22, 1994 [JP] Japan ..................... 6-084683

[51] Int. Cl.⁶ ............ A61K 31/505; C07D 239/02
[52] U.S. Cl. ................. 514/269; 514/256; 544/224; 544/242; 544/298; 544/315; 544/318; 544/321
[58] Field of Search ............... 514/269; 544/315, 544/318, 321

[56] References Cited

U.S. PATENT DOCUMENTS

| | | | |
|---|---|---|---|
| 4,329,488 | 5/1982 | Wenger et al. | |
| 5,071,860 | 12/1991 | Alig et al. | 514/332 |
| 5,102,903 | 4/1992 | Smith | 514/406 |
| 5,315,013 | 5/1994 | Carini et al. | 548/376.1 |

FOREIGN PATENT DOCUMENTS

| | | |
|---|---|---|
| 0388682A1 | 9/1990 | European Pat. Off. |
| 0530702A1 | 3/1993 | European Pat. Off. |
| 2273657 | 11/1990 | Japan. |
| WO9214714 | 9/1992 | WIPO. |

*Primary Examiner*—Jose' G. Dees
*Assistant Examiner*—Sabiha N. Qazi
*Attorney, Agent, or Firm*—Birch, Stewart, Kolasch & Birch, LLP

[57] ABSTRACT

There are disclosed novel ether compounds of the general formula:

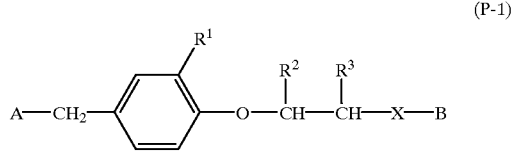

(P-1)

wherein $R^1$, $R^2$ and $R^3$ are each hydrogen or the like; A is a group of the general formula:

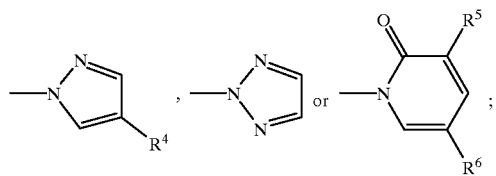

B is a group of the general formula:

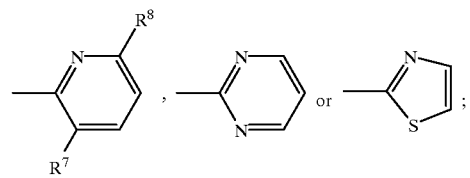

and X is oxygen or sulfur; and harmful-organism controlling agents containing them as active ingredients.

6 Claims, No Drawings

ETHER COMPOUNDS AND THEIR USE

This application is a divisional of application Ser. No. 08/727,565, filed on Dec. 6, 1996 now U.S. Pat. No. 5,883,262. Application Ser. No. 08/727,565 is the national phase of PCT International Application No. PCT/JP95/00763 filed on Apr. 19, 1995 under 35 U.S.C. § 371. The entire contents of each of the above identified applications are hereby incorporated by reference.

TECHNICAL FIELD

The present invention relates to ether compounds and their use. More particularly, the present invention relates to ether compounds which have excellent controlling effects against harmful organisms and to harmful-organism controlling agents containing them as active ingredients.

DISCLOSURE OF THE INVENTION

The present inventors have intensively studied to find compounds which have excellent controlling effects against harmful organisms. As a result, they have found that ether compounds of the general formula P-1 as depicted below have excellent controlling effects against harmful organisms, thereby completing the present invention.

Thus the present invention provides ether compounds (hereinafter referred to as the present compound(s)) of the general formula:

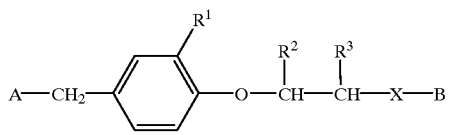

(P-1)

wherein $R^1$ is hydrogen or chlorine;
$R^2$ and $R^3$ are independently hydrogen or methyl;
A is a group of the general formula:

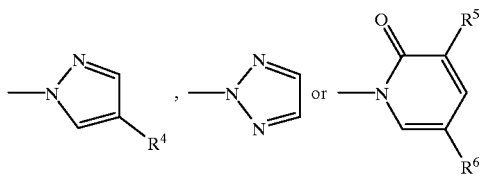

wherein $R^4$ is hydrogen, chlorine or methyl; and $R^5$ and $R^6$ are independently hydrogen or chlorine;
B is a group of the general formula:

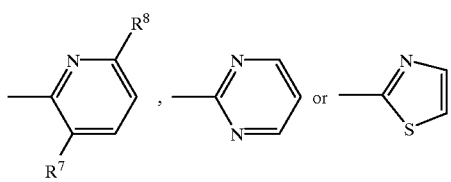

wherein $R^7$ and $R^8$ are independently hydrogen or fluorine; and
X is oxygen or sulfur; and harmful-organism controlling agents containing them as active ingredients.

EMBODIMENTS FOR MAKING THE INVENTION

In the present compounds, it is preferred from the viewpoint of harmful-organism controlling activity that A is a group of the general formula:

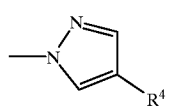

(P-2)

wherein $R^4$ is as defined above. Among them, a group wherein $R^4$ is hydrogen is preferred, and $R^1$ is preferably hydrogen.

The present compounds can be produced, for example, by the following processes.

(Production process a)

This is a production process in which a phenol derivative of the general formula:

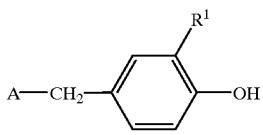

(P-3)

wherein $R^1$ and A are as defined above, with a compound of the general formula:

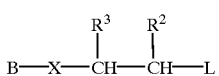

(P-4)

wherein $R^2$, $R^3$, B and X are as defined above; and L is halogen (e.g., chlorine, bromine, iodine), mesyloxy or tosyloxy.

(Production process b)

This is a production process in which a compound of the general formula:

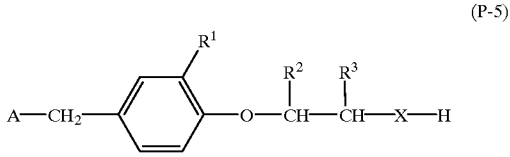

(P-5)

wherein $R^1$, $R^2$, $R^3$, A and X are as defined above, or an alkali metal salt thereof (e.g., lithium salt, sodium salt, potassium salt), is reacted with a compound of the general formula:

(P-6)

wherein B and L are as defined above.

(Production process c)

This is a production process in which a compound of the general formula:

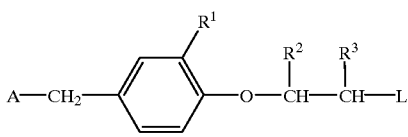

wherein $R^1$, $R^2$, $R^3$, A and L are as defined above, is reacted with a compound of the general formula:

wherein B and X are as defined above, or an alkali metal salt thereof (e.g., lithium salt, sodium salt, potassium salt).

In the production processes a, b and c, the reaction is preferably effected in the presence of a base without any solvent or in an inert organic solvent (however, when an alkali metal salt of the compound of the general formula P-5 or P-8 is used for the reaction in the production process b and c, there is no need to use a base).

This reaction is usually effected in an inert organic solvent. As the solvent which can be used, there can be mentioned, for example, aromatic hydrocarbons such as benzene, toluene, xylene and chlorobenzene; nitriles such as acetonitrile, propionitrile and isobutyronitrile; ketones such as acetone, methyl isobutyl ketone and methyl ethyl ketone; methanol, ethanol, n-propyl alcohol and the like; ethers such as methoxyethane, tetrahydrofuran and dioxane; polar solvents such as N,N-dimethylformamide, N,N-dimethylacetamide, dimethylsulfoxide, sulforane and hexamethylphosphoric triamide; water; or mixtures thereof. To make more smooth progress in the reaction, phase transfer catalysts may be added, such as benzyltriethylammonium chloride and tetra-n-butylammonium bromide.

As the base which can be used, there can be mentioned, for example, alkali metals such as sodium and potassium; alkali metal hydroxides such as sodium hydroxide and potassium hydroxide; alkali metal carbonates such as sodium carbonate and potassium carbonate; alkali metal hydrides such as sodium hydride; metal alkoxides such as sodium ethoxide and sodium methoxide; and organic bases such as pyridine, triethylamine, N,N-dimethylaniline and 4-N,N-dimethylaminopyridine.

In the production processes, a, b and c, although the reaction temperature is not particularly limited, the reaction is usually effected in the range of $-30°$ C. to $200°$ C. or the boiling point of the solvent used, preferably in the range of $20°$ C. to $110°$ C. The reaction time is usually 0.5 to 24 hours.

The molar ratio of the phenol derivative of the general formula P-3 to the compound of the general formula P-4, which are used in the production process a, is usually 1:0.5 to 2, preferably 1:0.7 to 1.5. The molar ratio of the compound of the general formula P-5 to the compound of the general formula P-6, which are used in the production process b, is usually 1:0.5 to 10, preferably 1:0.8 to 2. The molar ratio of the compound of the general formula P-7 to the compound of the general formula P-8, which are used in the production process c, is usually 1:1 to 10, preferably 1:1.1 to 1.5.

In the production processes a, b and c, after completion of the reaction, the reaction mixture is subjected to ordinary post-treatments such as extraction with an organic solvent and concentration. Thus the present compounds can be isolated. If necessary, purification may be carried out by recrystallization, column chromatography or the like.

Typical examples of the present compounds are shown below.

Compounds of the general formulas:

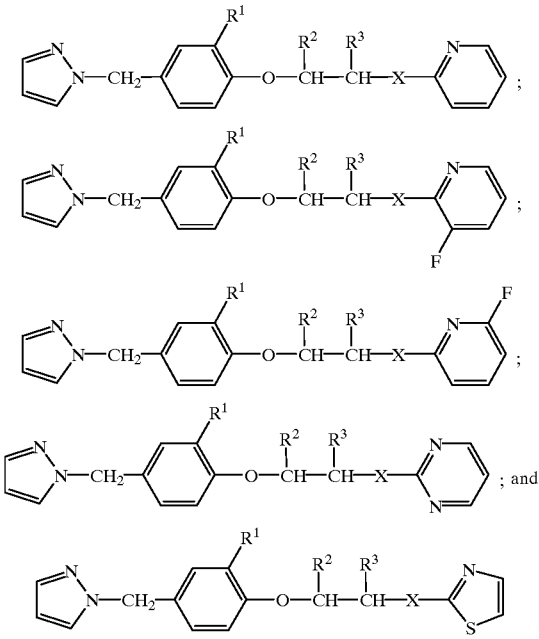

wherein $R^1$, $R^2$, $R^3$ and X are as defined in Table 1; and

TABLE 1

| $R^1$ | $R^2$ | $R^3$ | X | $R^1$ | $R^2$ | $R^3$ | X |
|---|---|---|---|---|---|---|---|
| H | H | H | O | H | H | H | S |
| Cl | H | H | O | Cl | H | H | S |
| H | H | CH$_3$ | O | H | H | CH$_3$ | S |
| H | CH$_3$ | H | O | H | CH$_3$ | H | S |
| H | CH$_3$ | CH$_3$ | O | H | CH$_3$ | CH$_3$ | S |
| Cl | H | CH$_3$ | O | Cl | H | CH$_3$ | S |
| Cl | CH$_3$ | H | O | Cl | CH$_3$ | H | S |
| Cl | CH$_3$ | CH$_3$ | O | Cl | CH$_3$ | CH$_3$ | S | those of the general formulas:

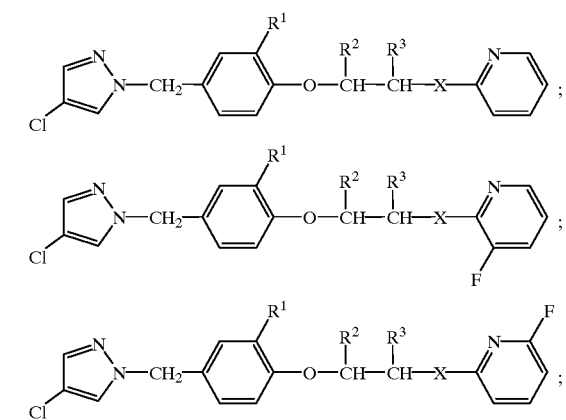

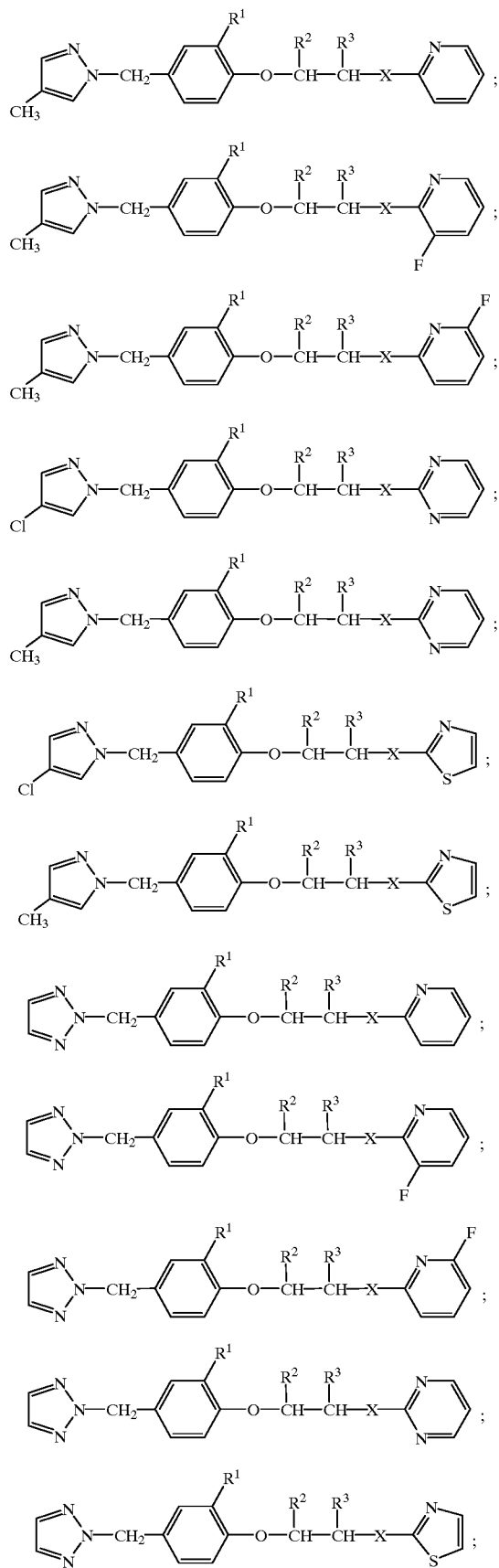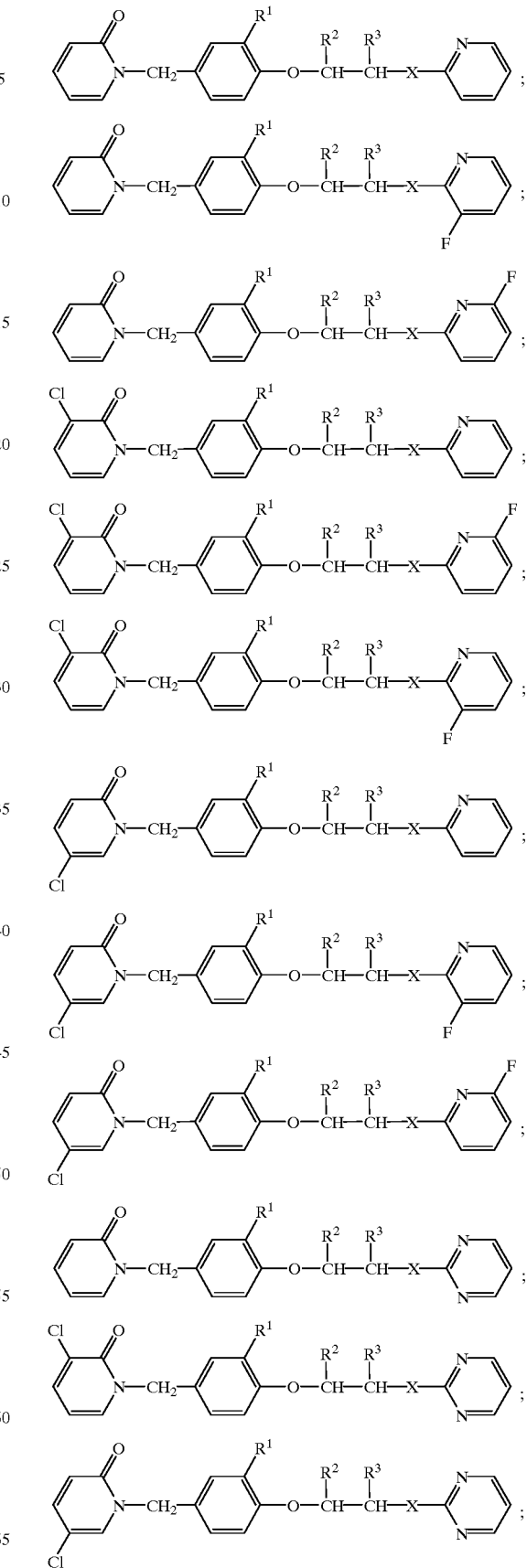

-continued

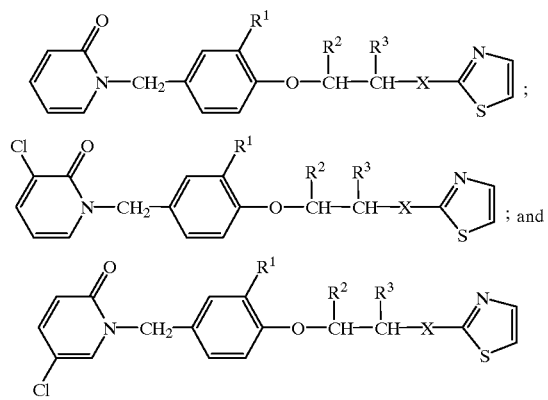

wherein $R^1$, $R^2$, $R^3$ and X are as defined in Table 2.

TABLE 2

| $R^1$ | $R^2$ | $R^3$ | X | $R^1$ | $R^2$ | $R^3$ | X |
|---|---|---|---|---|---|---|---|
| H | H | H | O | H | H | H | S |
| Cl | H | H | O | Cl | H | H | S |
| H | H | $CH_3$ | O | H | H | $CH_3$ | S |
| H | $CH_3$ | H | O | H | $CH_3$ | H | S |
| Cl | H | $CH_3$ | O | Cl | H | $CH_3$ | S |
| Cl | $CH_3$ | H | O | Cl | $CH_3$ | H | S |

The compounds of the general formulas P-4, P-6 and P-8, which are intermediates for use in the production of the present compounds, may be obtained from commercial sources; however, the compounds of the general formula P-4 can be produced, for example, according to the method described in Synthesis, 573 (1980), or the compounds of the general formula P-8 can be produced, for example, according to the method described in the publication JP-A 56-90059.

The compounds of the general formulas P-5 and P-7 can be produced, for example, from the compounds of the general formula P-3 through the following reaction scheme:

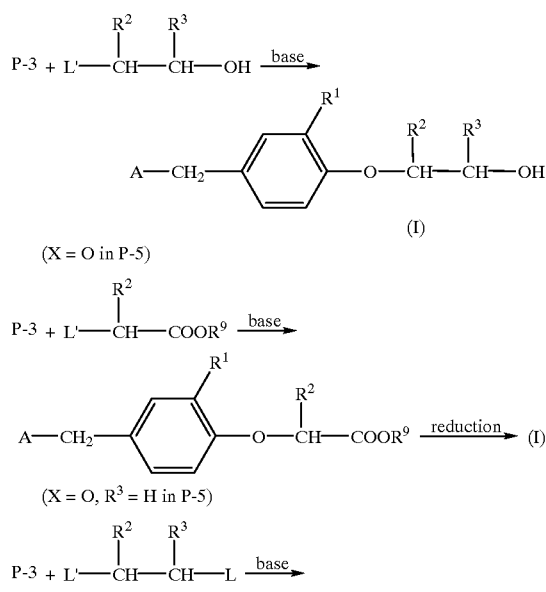

-continued

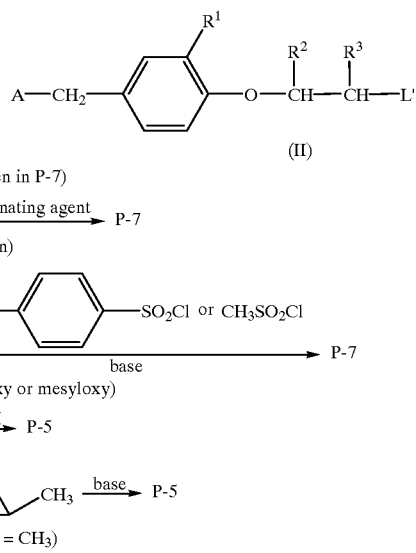

(L' = halogen in P-7)

(I) $\xrightarrow{\text{halogenating agent}}$ P-7

(L = halogen)

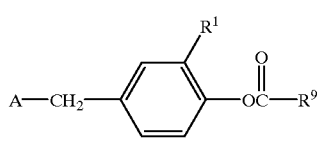

(I) $\xrightarrow[\text{base}]{}$ P-7

(L = tosyloxy or mesyloxy)

(II) $\xrightarrow{\text{NaSH}}$ P-5

(X = S)

P-3 + △—$CH_3$ $\xrightarrow{\text{base}}$ P-5

($R^2$ = H, $R^3$ = $CH_3$)

wherein $R^1$, $R^2$, $R^3$, A and L are as defined above; L' is halogen (e.g., chlorine, bromine, iodine); and $R^9$ is $C_1$–$C_4$ alkyl (e.g., methyl, ethyl).

The phenol derivatives of the general formula P-3 can be produced, for example, by the following process.

This is a process in which a phenol ester derivative of the general formula:

(P-9)

A—$CH_2$—⬡($R^1$)—O—C(=O)—$R^9$ wherein $R^1$ and A are as defined above and $R^9$ is $C_1$–$C_4$ alkyl (e.g., methyl, ethyl) or phenyl, is hydrolyzed under the basic conditions.

As the base which can be used, there can be mentioned, for example, alkali metal hydroxides such as sodium hydroxide and potassium hydroxide; alkaline earth metal hydroxides such as ballium hydroxide; alkali metal carbonates such as potassium carbonate and sodium carbonate.

This reaction is usually effected in a solvent. As the solvent which can be used, there can be mentioned, for example, alcohols such as methanol, ethanol, n-propyl alcohol, ethylene glycol and diethylene glycol; water; or mixtures thereof.

The reaction is usually effected in the range of 0° to 200° C. or the boiling point of the solvent used, preferably in the range of 20° to 120° C. The reaction time is usually 1 to 500 hours.

As the amounts of reagents to be used in the reaction, the base can be used at any mole to 1 mole of the phenol derivative of the general formula P-9, preferably at a ratio of 1 to 2 moles.

The phenol ester derivatives of the general formula P-9 can be produced, for example, by the following process.

This is a process in which a phenol ester compound of the general formula:

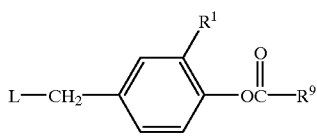

(P-10)

wherein $R^1$, $R^9$ and L are as defined above, is reacted with a compound of the general formula:

A—H           (P-I 1)

wherein A is as defined above, in the presence of a base.

This reaction is usually effected in an inert organic solvent. As the solvent which can be used, there can be mentioned, for example, aromatic hydrocarbons such as benzene, toluene, xylene and chlorobenzene; nitriles such as acetonitrile, propionitrile and isobutyronitrile; ketones such as acetone, methyl isobutyl ketone and methyl ethyl ketone; alcohols such as methanol, ethanol and n-propyl alcohol; ethers such as diethyl ether, diisopropyl ether, 1,2-dimethoxyethane, tetrahydrofuran and dioxane; polar solvents such as N,N-dimethylformamide, N,N-dimethylacetamide, dimethylsulfoxide, sulforane and hexamethylphosphoric triamide; or mixtures thereof.

As the base which can be used, there can be mentioned, for example, alkali metals such as sodium and potassium; alkali metal hydroxides such as sodium hydroxide and potassium hydroxide; alkali metal carbonates such as sodium carbonate and potassium carbonate; alkali metal hydrides such as sodium hydride; alkali metal alkoxides (e.g., $C_1$–$C_4$ alkoxides such as methoxides and ethoxides) such as sodium ethoxide and sodium methoxide; and organic bases such as pyridine, triethylamine, N,N-dimethylaniline and 4-N,N-dimethylaminopyridine.

The reaction is usually effected in the range of 0° to 200° C. or the boiling point of the solvent used, preferably in the range of 20° to 120° C. The reaction time is usually 1 to 50 hours.

The amounts of reagents to be used in the reaction are usually in the ratio of 1 to 10 moles, preferably 1 to 2 moles, for each of the compound of the general formula P- 11 and the base, to 1 mole of the phenol ester compound of the general formula P-10.

The present compounds exhibit excellent controlling effects against harmful organisms, for example, noxious insects and noxious ticks and mites, such as described below:

Noxious insects of Hemiptera planthoppers (Delphacidae) such as brown rice planthopper (*Nilaparvata lugens*), white-backed rice planthopper (*Sogatella furcifera*) and small brown planthopper (*Laodelphax striatellus*); leafhoppers (Deltocephalidae) such as green rice leafhopper (*Nephotettix cincticeps*), green rice leafhopper (*Nephotettix virescens*), green rice leafhopper (*Nephotettix nigropictus*), zig-zag rice leafhopper (*Recilia dorsalis*), tea green leafhopper (*Empoasca onukii*) and grape leafhopper (*Arboridia apicalis*); aphids (Aphididae) such as cotton aphid (*Aphis gossypii*) and green peach aphid (*Myzus persicae*); stink bugs (Pentatomidae); whiteflies (Aleyrodidae) such as sweetpotato whitefly (*Bemisia tabaci*) and greenhouse whitefly (*Trialeurodes vaporariorum*); scale insects (Coccidae); lace bugs (Tingidae); psyllids (Psyllidae), etc.

Noxious insects of Lepidoptera pyralid moths (Pyralidae) such as rice stem borer (*Chilo suppressalis*), rice leafroller (*Cnaphalocrocis medinalis*) and Indian meal moth (*Plodia interpunctella*); owlet moths (Noctuidae) such as common cutworm (*Spodoptera litura*), rice armyworm (*Spodoptera exigua*) and cabbage armyworm (*Mamestra brassicae*); white and sulfer butterflies (Pieridae) such as common cabbageworm (*Pieris rapae crucivora*); tortricid moths (Tortricidae) such as Adoxophyes spp.; Carposinidae; lionetiid moths (Lyonetiidae); leafblotch miners (Graciltariidae); gelechiid moths (Gelechiidae); tussock moths (Lymantrnidae); Plusiae; *Agrotis* spp. such as cutworm (*Agrotis segetum*) and black cutworm (*Agrotis ipsilon*); *Heliothis* spp.; diamondback moth or cabbage moth (*Plutelia xylostella*); casemaking clothes moth or case-bearing dothes moth (*Tinea pellionella*); webbing clothes moth or common clothes moth (*Tineola bisselliella*), etc.

Noxious insects of Diptera mosquitos (Calicidae) such as coiimmon mosquito (*Culex pipiens pallens*) and *Cules tritaeniorhynchus*; *Aedes* spp. such as *Aedes aegypti* and *Aedes albopictus*; *Anopheles* spp. such as *Anophelinae sinensis*; midges (Chironomidae); house flies (Muscidae) such as house fly (*Musca domestica*) and false stablefly (*Muscina stabulans*); Calliphoridae; Sarcophagidae; anthomyild flies (Anthomyiidae) such as lesser housefly (*Fannia canicularis*), seedcorn maggot (*Hylemya platura*) and onion maggot (*Hylemya antique*); gall midges (Cecidomyiidae); fruit flies (Tephritidae); shore flies (Ephydridue); small fruit flies (Drosophilidae); moth flies (Psychodidae); black flies (Simulii- dae); Tabanidae; stable flies (Stomoxyidae), etc.

Noxious insects of Coleoptera corn rootworms such as western corn rootworm (*Diabrotica virgifera*) and southern corn rootworm (*Diabrotica undecimpunctata*); scarabs (Scarabaeidae) such as cupreous chafer (*Anomala cuprea*) and soybean beetle (*Anomala rufocuprea*); weevils (Curculionidae) such as maize weevil (*Sitophilus zeamais*), rice water weevil (*Lissorphoptrus oryzophilus*) and azuki bean weevil (*Calosobruchys chinensis*); darkling beetles (Tenebrionidae) such as yellow mealworm (*Tenebrio molitor*) and red flour beetle (*Tribolium castaneum*); lef beetles (Chrysomelidae) such as striped flea beetle (*Phyllotreta striolata*) and cucurbit leaf beetle (*Aulacophora femoralis*); drugstore beetles (Anobiidae); *Epilachna* spp. such as twenty-eight-spotted ladybird (*Epilachna vigintioctopunctata*); powder post beetles (Lyctidae); false powderpost beetles (Bostrychidae); longhorn beetles (Cerambycidae), etc.

Noxious insects of Dictyoptera

German cockroach (*Blattella germanica*), smokybrown cockroach (*Peripineta fuliginosa*), American cockroach (*Peroplaneta americana*), brown cockroach (*Periplaneta brunnea*), oriental cockroach (Blatta orientalis), etc.

Noxius insects of Thysanoptera

*Thrips palmi*, yellow tea thrips (*Scirtothrips dorsalis*), flower thrips (*Thrips hawaiiensis*), etc.

Noxious insects of Hymenoptera ants (Formicidae); sawflies (Tenthredinidae) such as cabbage sawfly (*Athalia rosae japonensis*), etc.

Noxious insects of Orthoptera mole crickets (Gryllotalpidae), grasshoppers (Acrididae), etc.

Noxious insects of Aphaniptera

*Purex irritans* etc.

Noxious insects of Anoplura

*Pediculus humanus capitis, Phthirus pubis,* etc.

Noxious insects of Isoptera

*Reticulitermes speratus,* Formosan subterranean termite (*Coptotennes formosanus*), etc.

Spider mites (Tetranychidae)

carmine spider mite (*Tetranychus cinnabarinus*), two-spotted spider mite (*Tetranychus urticae*), Kanzawa spider mite (*Tetranychus kazawai*), citrus red mite (*Panonychus citri*), fruit tree red spider mite (*Panonychus ulmi*), etc.

Ticks (Ixodidae)

*Boophilus microphus* etc.

House dust mites

Grain mites, Dermatophagoides, Cheyletid mites, Ornitonyssus, etc.

If the present compounds are used in combination with other insecticides and/or acaricides, the controlling effects achieved by the present compounds can find practical applications to more various places for use against a wider variety of noxious insects.

As the insecticide and/or acaricide, which are suitable for combined use, there can be mentioned, for example, organophosphorus compounds such as Fenitrothion [O,O-dimethyl O-(3-methyl-4-nitrophenyl)phosphorothioate], Fenthion [O,O-dimethyl O-(3-methyl-4(methylthio)phenyl]phosphorothioate], Diazinon [O,O-diethyl-O-2-isopro-pyl-6-methylpyrimidin-4-ylphosphorothioate], Chlorpyriphos [O,O-diethyl-O-3,5,6-trichloro-2-pyridylphosphorothioate], Acephate [O,S-dimethylacetylphosphoramidothioate], Methidathion [S-2,3-dihydro-5-methoxy-2-oxo-1,3,4-thiadiazol-3-ylmethyl O,O-dimethylphosphorodithioate], Ethylthiometon [O,O-diethyl S-2-ethylthioethylphosphorodithioate], DDVP [2,2-dichlorovinyldimethylphosphate], Sulprofos [O-ethyl O-4-(methylthio)phenyl S-propylphosphorodithioate], Cyanophos [O-4-cyanophenyl O,O-dimethylphosphorothioate], Salithion [2-methoxy-4H-1,3,2-benzodioxaphosphinine-2-sulfide], Dimethoate [O,O-dimethyl-S-(N-methylcarbamoylmethyl)dithiophosphate], Phenthoate [ethyl 2-dimethoxyphosphinothioylthio(phenyl)acetate], Malathion [diethyl(dimethoxyphosphinothioylthio)succinate], Trichlorfon [dimethyl 2,2,2-trichloro-1-hydroxyethylphosphonate], Azinphos-methyl [S-3,4-dihydro-4-oxy-1,2,3-benzotriazin-3-ylmethyl O,O-dimethylphosphorodithioate] and Monocrotophos [dimethyl (E)-1-methyl-2-(methylcarbamoyl)vinylphosphate]; carbamate compounds such as BPMC [2-sec-butylphenylmethylcarbamate], Benfuracarb [ethyl N-[2,3-dihydro-2,2-dimethylbenzofuran-7-yloxycarbonyl(methyl)aminothio]-N-isopropyl-β-alaninate], Propoxur [2-isopropoxyphenyl N-methylcarbamate], Carbosulfan [2,3-dihydro-2,2-dimethyl-7-benzo[b]furanyl N-dibutylaminothio-N-methylcarbamate], Carbaril [1-naphthyl-N-methylcarbamate], Methomyl [S-methyl-N-[(methylcarbamoyl)oxy]thioacetirdate], Ethiofencarb [2-(ethylthiomethyl)-phenylmethylcarbamate], Aldicarb [2-methyl-2-(methylthio)propanaldehyde O-methylcarbamoyloxime] and Oxamyl [N,N-dimethyl-2-methylcarbamoyloxyimino-2-(methylthio)acetamide]; pyrethroid compounds such as Etofenprox [2-(4-ethoxyphenyl)-2-methylpropyl-3-phenoxybenzylether], Fenvalerate [(RS)-α-cyano-3-phenoxybenzyl (RS)-2-(4-chlorophenyl)-3-methylbutyrate], Esfenvalerate [(S)-α-cyano-3-phenoxybenzyl (S)-2-S)-α-cyano-3-phenoxybenzyl 2,2,3,3-tetramethylcyclopropanecarboxylate], Cypermethrin [(RS)-α-cyano-3-phenoxybenzyl (1RS,3RS)-3-(2,2-dichlorovinyl)-2,2-dimethylcyclopropanecarboxylate], Permethrin [3-phenoxybenzyl (1RS,3RS)-(1RS,3RS)-3-(2,2-dichlorovinyl)-2,2-methylcyclopropanecarboxylate], Cyhalothrin [(RS)-α-cyano-3-phenoxybenzyl (Z)-(1RS)-3-(2-chloro-3,3,3-trifluoropropenyl)-2,2-dimethylcyclopropanecarboxylate], Deltamethrin [(S)-(α-cyano-m-phenoxybenzyl (1R,3R)-3-(2,2-dibromovinyl)-2,2-dimethylcyclopropanecarboxylate] and Cyloprothrin [(RS)-α-cyano-3-phenoxybenzyl (RS)-2,2-dichloro- 1-(4-ethoxyphenyl)cyclopropanecarboxylate]; thiadiazine derivatives such as Buprofezin [2-tert-butylimino-3-isopropyl-5-phenyl-1,3,5-thiadiazin-4-one]; nitroimidazolidine derivatives such as Imidacloprid [1-(6-chloro-3-pyridylmethyl)-N-nitroirnidazolidin-2-ylidenamine]; Nereistoxin derivatives such as Cartap [S,S'-(2-dimethylaminotrimethylene)bis(thiocarbamate)], Thiocyclam [N,N-dimethyl-1,2,3-trithian-5-ylaniine] and Bensultap [S,S'-2-direthylaminotrimethylene di(benzenethiosulfonate)]; chlorinated hydrocarbon compounds such as Endosulfan [6,7,8,9,10, 10-hexachloro- 1,5,5a,6,9 ,9a-hexahydro-6 ,9-methan o-2,4,3-benzodioxathiepinoxide] and γ-BHC [1,2,3,4,5,6-hexachlorocyclohexane]; benzoylphenylurea compounds such as Chlorfluazuron [1-(3,5-dichloro-4-(3-chloro-5-trifluoromethylpyridin-2-yloxy)phenyl)-3-(2,6-difluorobenzoyl)urea], Teflubenzuron [1-(3,5-dichloro-2,4-difluorophenyl)-3-(2,6-difluorobenzoyl)urea] and Fulphenoxron [1-(4(2-chloro-4trifluoromethylphenoxy)-2-fluorophenyl)-3-(2,6-difluorobenzoyl)urea]; formamidine derivatives such as Amitraz [N,N' [(methylimino)dimethylidine]-di-2,4-xylidine] and Chlordimeform [N'-(4-chloro-2-methylphenyl)-N,N-dimethylmethanimidamide].

When used as the active ingredients of harmful-organism controlling agents, the present compounds, although they may be used as such without any addition of other ingredients, are usually used as formulations such as oil sprays, emulsifiable concentrates, wettable powders, flowable concentrates for water-based suspensions or water-based emulsions; granules, dusts, aerosols, heating fumigants, e.g., fumigants of the self-combustion type, chemical reaction type or porous ceramic plate type; ULV agents or poison baits, by mixing them with solid carriers, liquid carriers, gaseous carriers or baits, and, if necessary, adding surfactants and other adjuvants for use in formulation.

These formulations contain the present compounds as the active ingredients usually in a proportion of from 0.001% to 95% by weight.

As the solid carrier to be used for formulation, there can be mentioned, for example, fine powder or granules of clay materials (e.g., kaolin clay, diatomaceous earth, synthetic hydrated silicon oxide, bentonite, Fubasarni clay, acid clay), various kinds of talc, ceramics and other inorganic minerals (e.g., sericite, quartz, sulfur, active carbon, calcium carbonate, hydrated silica) and chemical fertilizers (e.g., ammonium sulfate, ammonium phosphate, ammonium nitrate, urea, ammonium chloride). As the liquid carrier, there can be mentioned, for example, water, alcohols (e.g., methanol, ethanol), ketones (e.g., acetone, methyl ethyl ketone), aromatic hydrocarbons (e.g., benzene, toluene, xylene, ethylbenzene, methylnaphthalene), aliphatic hydrocarbons (e.g., hexane, cyclohexane, kerosine, gas oil), esters (e.g., ethyl acetate, butyl acetate), nitriles (e.g., acetonitrile, isobutyronitrile), ethers (e.g., diisopropyl ether, dioxane), acid amides (e.g., N,N-dimethylformamide, N,N-dimethylacetamide), halogenated hydrocarbons (e.g., dichloromethane, trichloroethane, carbon tetrachloride), dimethyl sulfoxide and vegetable oils (e.g., soybean oil, cottonseed oil). As the gaseous carrier or propellant, there can be mentioned, for example, flon gas, butane gas, LPG (liquefied petroleum gas), dimethyl ether and carbon dioxide.

As the surfactant, there can be mentioned, for example, alkyl sulfates, alkyl sulfonates, alkyl arylsulfonates, alkyl aryl ethers and their polyoxyethylene derivatives, polyethylene glycol ethers, polyhydric alcohol esters and sugar alcohol derivatives.

As the adjuvant for use in formulation, such as fixing agents or dispersing agents, there can be mentioned, for example, casein, gelatin, polysaccharides (e.g., starch powder, gum arabic, cellulose derivatives, alginic acid), lignin derivatives, bentonite, sugars and synthetic water-soluble polymers (e.g., polyvinyl alcohol, polyvinyl pyrrolidone, polyacrylic acid). As the stabilizer, there can be mentioned, for example, PAP (isopropyl acid phosphate), BHT (2,6-di-tert-butyl-4-methylphenol), BHA (mixtures of 2-tert-butyl4-methoxyphenol and 3-tert-butyl-4-methoxyphenol), vegetable oils, mineral oils, surfactants, fatty acids or their esters.

As the base material for fumigants of the self-combustion type, there can be mentioned, for example, combustion heat-generating agents such as nitrate salts, nitrite salts, guanidine salts, potassium chlorate, nitrocellulose, ethyl cellulose and wood powder; thermolysis stimulators such as alkali metal salts, alkaline earth metal salts, dicromates and cromates; oxygen suppliers such as potassium nitrate; combustion aids such as melamine and wheat starch; extending agents such as diatomaceous earth; and binders such as synthetic paste.

As the base material for fumigants of the chemical reaction type, there can be mentioned, for example, exothermic agents such as sulfides, polysulfides, hydrosulfides and salt hydrates of alkali metals, and calcium oxide; catalytic agents such as carbonaceous materials, iron carbide and activated clay; organic foaming agents such as azodicarbonamide, benzenesulfonyl hydrazine, dinitropentamethylenetetramine, polystyrene and polyurethane; and fillers such as natural fiber chips and synthetic fiber chips.

As the base material for poison baits, there can be mentioned, for example, bait ingredients such as grain powder, vegetable oils, sugars and crystalline cellulose; antioxidants such as dibutylhydroxytoluene and nordihydroguaiaretic acid; preservatives such as dehydroacetic acid; feeding-error preventing agents such as red pepper powder; and attractant flavors such as cheese flavor and onion flavor.

The formulations such as flowable concentrates (for water-based suspensions or water-based emulsions) are usually obtained by suspending 1–75% compound in water containing 0.5–15% dispersing agents, 0.1–10% suspending agents (e.g., protective colloids or thixotropy-imparting compounds) and 0–1.0% appropriate adjuvants (e.g., defoaming agents, anti-corrosive agents, stabilizing agents, spreading agents, penetration aids, anti-freezing agents, anti-fungus agents, anti-smoking agents). Various oils in which the present compounds are substantially insoluble may be used instead of water to give oil-based suspensions. As the protective colloid, there can be mentioned, for example, gelatin, casein, various kinds of gum, cellulose ethers and polyvinyl alcohol. As the thixotropy-imparting compound, there can be mentioned, for example, bentonite, aluminum magnesium silicate, xanthane gum and polyacrylic acid.

The formulations thus obtained are used as such or after diluted with water or the like. They may be used, in admixture or without mixing, with other insecticides, nematocides, acaricides, fungicides, herbicides, plant growth regulators, synergists, fertilizers, soil conditioners, animal feed and the like.

When the present compounds are used as the harmful-organism controlling agents for agriculture, the application amount thereof is usually in the range of 0.001 to 500 g, preferably 0.1 g to 500 g, per 10 ares. Their formulations such as emulsifiable concentrates, wettable powders and flowable concentrates are usually used after diluted with water to an application concentration of 0.0001 to 1000 ppm. Their formulations -.such as granules and dusts are used as such without any dilution. When the present compounds are used as the harmful-organism controlling agents for epidemic prevention, their formulations such as emulsifiable concentrates, wettable powders and flowable concentrates are usually used after diluted with water to an application concentration of 0.0001 to 10000 ppm, and their formulations such as oil sprays, aerosols, fumigants, ULV agents and poison baits are used as such.

All of these application amounts and application concentrations may vary with the formulation type, application time, application place, application method, kind of harmful organisms such as noxious insects, noxious mites and ticks, degree of damage and other conditions, and they can be increased or decreased without limitation to the above range.

EXAMPLES

The present invention will be further illustrated by the following production examples, formulation examples and test examples; however, the present invention is not limited to these examples.

Production Example 1 Production of compound 1 by production process a

To a mixture of 10 ml of anhydrous N,N-dimethylformamide and 72 mg of sodium hydride (60% oil dispersion) was added dropwise an anhydrous N,N-dimethyl-formamide (5 ml) solution of 300 mg of 4-(1-pyrazolyl)methylphenol under stirring over 10 minutes. After stirring at room temperature for 1 hour, the mixture was cooled to 5° to 10° C., to which an anhydrous N,N-dimethylformamide (5 ml) solution of 505 mg of 2-(2-pyridyloxy)ethyl p-toluenesulfonate was added dropwise over 30 minutes. The mixture was stirred at room temperature overnight and then at 60° to 70° C. for further 2 hours. The reaction mixture was poured into 50 ml of ice water, which was extracted twice with 30 ml of ethyl acetate. The organic layers were combined, washed with water, dried with anhydrous magnesium sulfate, and concentrated under reduced pressure. The residue was subjected to silica gel column chromatography, which afforded 208 mg of 4-(1-pyrazolyl)methylphenyl 2-(2-pyridyloxy)ethyl ether (compound 1). Yield, 41%.

m.p., 82.7° C.

Production Example 2 Production of compound 2 by production process b

To a mixture of 10 ml of anhydrous N,N-dimethylformamide and 96 mg of sodium hydride (60% oil dispersion) was added dropwise an anhydrous N,N-dimethyl-formamide (5 ml) solution of 500 mg of 2-[4-(1-pyrazolyl)methylphenoxy]ethanol (produced in Reference Production Example 1 described below) under stirring over 10 minutes. After stirring at 60° to 70° C. for 2 hours, the mixture was cooled to 5° to 10° C., to which an anhydrous N,N-dimethylformamide (5 ml) solution of 288 mg of 2-chloropyrimidine was added dropwise over 30 minutes. The mixture was then stirred at room temperature overnight and then at 60° to 70° C. for further 2 hours. The reaction mixture was poured into 50 ml of ice water, which was extracted with twice with 30 ml of toluene. The organic layers were combined, washed with water, dried with anhydrous magnesium sulfate, and concentrated under reduced pressure. The residue was subjected to silica gel column chromatography, which afforded 339 mg of 4-(1-pyrazolyl) methyl-phenyl 2-(2-pyrimidyloxy)ethyl ether (compound 2). Yield, 50%.

m.p., 81.7° C.

Production Example 3 Production of compound 3 by production process c

To a mixture of 5 ml of anhydrous N,N-dimethylformamide and 51 mg of sodium hydride (60% oil dispersion) is added dropwise an anhydrous N,N-dimethylformamide (3 ml) solution of 121 mg of 2-hydroxypyridine under stirring over 10 minutes. After stirring at room temperature for 1 hour, the mixture is cooled to 5° to 10° C., to which an anhydrous N,N-dimethylformamide (2 ml) solution of 300 mg of 2-[4-(2-2H-1,2,3-triazolyl)methylphenoxy]ethyl bromide is added dropwise over 30 minutes. The mixture is then stirred at room temperature overnight. The reaction mixture is poured into 50 ml of ice water, which is extracted with twice with 30 ml of toluene. The organic layers are combined, washed with water, dried with anhydrous magnesium sulfate, and concentrated under reduced pressure. The residue is subjected to silica gel column chromatography, which affords 4-(2-2H-1,2,3-triazolyl)methylphenyl 2-(2-pyridyloxy)ethyl ether.

Production Example 4 Production of compound 5 by production process b

To a mixture of 10 ml of anhydrous N,N-dimethylformamide and 110 mg of sodium hydride (60% oil dispersion) was added dropwise an anhydrous dimethylsulfoxide (5 ml) solution of 500 mg of 2-[4-(1-pyrazolyl) methylphenoxy]ethanol (produced in Reference Production Example 1 described below) under stirring over 10 minutes. After stirring at 60° to 70° C. for 2 hours, the mixture was cooled to 5° to 10° C., to which an anhydrous N,N-dimethylformamide (5 ml) solution of 488 mg of 2-bromothiazole was added dropwise over 10 minutes. The mixture was then stirred at room temperature overnight and then at 60° to 70° C. for further 2 hours. The reaction mixture was poured into 50 ml of ice water, which was extracted with twice with 30 ml of toluene. The organic layers were combined, washed with water, dried with anhydrous magnesium sulfate, and concentrated under reduced pressure. The residue was subjected to silica gel column chromatography, which afforded 280 mg of 4-(1-pyrazolyl) methylphenyl 2-(2-thiazolyloxy)ethyl ether (compound 5). Yield, 41%.

m.p., 65.6° C.

Production Example 5 Production of compound 8 by production process b

To a mixture of 10 ml of anhydrous N,N-dimethylformamide and 24 mg of sodium hydride (60% oil dispersion) was added dropwise an anhydrous N,N-dimethylformamide (5 ml) solution of 500 mg of 2-[2-chloro-4-(l-pyrazolyl)methylphenoxy]-ethanol (produced in Reference Production Example 3 described below) under stirring over 10 minutes. After stirring at 60° to 70° C. for 2 hours, the mixture was cooled to 5° to 10° C., to which an anhydrous N,N-dimethylformamide (5 ml) solution of 250 mg of 2-fluoropyridine was added dropwise over 30 minutes. The mixture was then stirred at room temperature overnight and then at 60° to 70° C. for further 2 hours. After completion of the reaction, the reaction mixture was poured into 50 ml of ice water, which was extracted with twice with 30 ml of toluene. The organic layers were combined, washed with water, dried with anhydrous magnesium sulfate, and concentrated under reduced pressure. The residue was subjected to silica gel column chromatography, which afforded 595 mg of 2-chloro-4-(1-pyrazolyl)methylphenyl 2-(2-pyridyloxy)ethyl ether (compound 8). Yield, 91%.

m.p., 82.3° C.

Some typical examples of the present compounds are shown with their compound numbers and physical properties in Table 3 (by the definition of each substituent in the compounds of the general formula P-1).

TABLE 3

Compounds of the general formula:

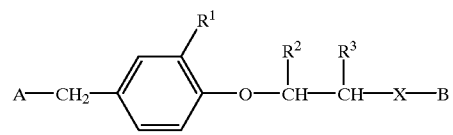

| Compound No. | A | R¹ | R² | R³ | X | B | Physical properties |
|---|---|---|---|---|---|---|---|
| 1 | pyrazolyl | H | H | H | O | 2-pyridyl | m.p. 82.7° C. |
| 2 | pyrazolyl | H | H | H | O | 2-pyrimidyl | m.p. 81.7° C. |
| 3 | 1,2,3-triazolyl | H | H | H | O | 2-pyridyl | m.p. 120.1° C. |

TABLE 3-continued

Compounds of the general formula:

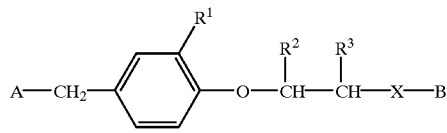

| Compound No. | A | R¹ | R² | R³ | X | B | Physical properties |
|---|---|---|---|---|---|---|---|
| 4 | Cl-pyrazolyl | H | H | H | O | 2-pyridyl | m.p. 84.1° C. |
| 5 | pyrazolyl | H | H | H | O | 2-thiazolyl | m.p. 65.6° C. |
| 6 | pyrazolyl | Cl | H | H | O | 2-pyrimidinyl | $n_D^{20.8}$ 1.5878 |
| 7 | pyrazolyl | Cl | H | H | O | 2-thiazolyl | $n_D^{20.8}$ 1.5925 |
| 8 | pyrazolyl | Cl | H | H | O | 2-pyridyl | m.p. 82.3° C. |
| 9 | pyrazolyl | H | H | CH₃ | O | 2-pyridyl | $n_D^{28.6}$ 1.5638 |
| 10 | pyrazolyl | H | CH₃ | H | O | 2-pyridyl | $n_D^{28.1}$ 1.5684 |

The following will describe production examples for the starting compounds used for the production of the present compounds.

Reference Production Example 1

A mixture of 60 g of 4-(1-pyrazolyl)methylphenol, 54.9 g of ethyl chloroacetate, 95.1 g of potassium carbonate, and 500 ml of anhydrous dimethylformamide was heated at 50° C. under stirring for 5 hours, followed by cooling to room temperature. The reaction mixture was poured into 1 liter of water, which was extracted twice with 200 ml of ethyl acetate. The organic layers were combined, washed with water, saturated aqueous ammonium chloride solution and then saturated sodium chloride solution, dried with anhydrous magnesium sulfate, and concentrated under reduced pressure to give crude ethyl 4-(1-pyrazolyl) methylphenoxyacetate as an oil.

To a suspension of 38 g of lithium aluminum hydride in 500 ml of anhydrous tetrahydrofuran was added dropwise a solution of the above crude ethyl 4-(1-pyrazolyl)-methylphenoxyacetate dissolved in 100 ml of anhydrous tetrahydrofuran at −78° C. under stirring over 30 minutes. The mixture was stirred at the same temperature for 1 hour and then at −20° C. for further 2 hours. The reaction mixture was cooled again to −78° C., to which 38 ml of water, 38 ml of 15% aqueous sodium hydroxide solution and then 114 ml of water were added dropwise at the same temperature and subsequently 500 ml of toluene, 500 ml of tetrahydrofuran and then 200 g of anhydrous sodium sulfate were added, and the mixture was stirred at room temperature for 2 hours. The reaction mixture was filtered through celite, and the filtrate was concentrated under reduced pressure. The residue was subjected to silica gel chromatography, which afforded 64.5 g of 2-[4-(pyrazolyl)methylphenoxy]ethanol as white crystals. Yield, 86% (based upon 4-(1-pyrazolyl)-methylphenol).

m.p., 56° to 58° C.

Reference Production Example 2

Production of 2-chloro-4-(1-pyrazolyl)methylphenol (1) Production of 2-chloro4-methylphenyl 2,2-dimethylpropanoate To a mixture of 100 g of 2-chloro-4-methylphenol, 92.3 g of triethylamine and 1 liter of anhydrous tetrahydrofuran was added dropwise 93.0 g of pivaloyl chloride at 5° to 10° C. under stirring over 1 hour. Then, after stirring at the same temperature for 3 hours, the reaction mixture was poured into ice water, which was extracted with diethyl ether. The organic layer was washed with 3% aqueous hydrochloric acid and then water, dried with anhydrous magnesium sulfate, and concentrated under reduced pressure. The resulting oil was distilled under reduced pressure, which afforded 155.3 g of 2-chloro4-methylphenyl 2,2-dimethylpropanoate as a colorless clear liquid. Yield, 97.7%.

b.p., 113–118° C./5 mmHg; $n_D^{21.8}$ 1.4949

(2) Production of 4-bromomethyl-2-chlorophenyl 2,2-dimethylpropanoate

To a mixture of 50.0 g of 2-chloro-4methylphenyl 2,2-dimethylpropanoate, 23.8 g of anhydrous sodium carbonate and 500 ml of carbon tetrachloride was added a very small amount of benzoyl peroxide and 35.2 g of bromine was added dropwise at 60° C. under stirring over 3 hours. While checking the progress of the reaction (the red color of bromine disappeared), a very small amount of benzoyl peroxide was added, if necessary, and stirring was continued until the reaction was thoroughly completed.

After completion of the reaction, the reaction mixture was cooled to 10° C., and undissolved matters were removed by filtration under suction, followed concentration under reduced pressure, which afforded 68.7 g of 4-bromomethyl 2-chlorophenyl 2,2-dimethylpropanoate as a pale yellow solid. Apparent yield, 101.7%. This solid was recrystallized from a mixed solvent of hexane and toluene to give white crystals.

m.p., 63.3° C.

(3) Production of 2-chloro-4-(1-pyrazolyl)methylphenyl 2,2-dimethylpropanoate

A mixture of 15.3 g of pyrazole, 89.9 g of sodium hydride (60% oil dispersion) and 200 ml of anhydrous N,N-dimethylformamide was stirred at 60° to 70° C. under a nitrogen atmosphere for 2 hours. After the evolution of hydrogen gas ceased, the mixture was cooled to 10° C. To this mixture was added dropwise an anhydrous N,N-dimethylformamide (300 ml) solution of 68 g of 4-bromomethyl-2-chlorophenyl 2,2-dimethylpropanoate at room temperature under stirring over 1 hour, and the mixture was stirred at 80° C. for 1 hour. After cooling, the mixture was poured into ice water, which was extracted with ethyl acetate. The organic layer was washed with saturated aqueous ammonium chloride solution and then saturated sodium chloride solution, dried with anhydrous magnesium sulfate, and concentrated under reduced pressure. The residue was subjected to silica gel column chromatography, which afforded 39.5 g of 2-chloro4-(1-pyrazolyl)methylphenyl 2,2-dimethylpropanoate as a colorless oil. Yield, 60%.

$n_D^{21.8}$ 1.5461

(4) Production of 2-chloro-4-(1-pyrazolyl)methylphenol

A mixture of 20.0 g of 2-chloro-4-(1-pyrazolyl)methylphenyl 2,2-dimethylpropanoate, 50 ml of 20% aqueous sodium hydroxide solution and 300 ml of ethanol was heated at reflux for 5 hours. The reaction mixture was then concentrated under reduced pressure, to which water was added, and the mixture was adjusted to pH 6.0 with concentrated hydrochloric acid. This mixture was extracted with ethyl acetate. The organic layer was washed with water, dried with anhydrous magnesium sulfate, and concentrated under reduced pressure. The residue was subjected to silica gel column chromatography, which afforded 11.5 g of 2-chloro-4-(1-pyrazolyl)methylphenol as white crystals. Yield, 80.7%.

m.p., 152.9° C.

Reference Production Example 3

Production of 2-[2-chloro-4-(1-pyrazolyl)methylphenoxy]ethanol

A mixture of 5.0 g of 2-chloro-4-(1-pyrazolyl)methylphenol (produced in Reference Production Example 2), 7.6 g of ethyl chloroacetate, 13.2 g of potassium carbonate and 100 ml of anhydrous dimethylformamide was heated at 50° C. under stirring for 5 hours, and then cooled to room temperature. The reaction mixture was poured into 500 ml of water, which was extracted twice with 50 ml of ethyl acetate. The organic layers were combined, washed with water, saturated aqueous ammonium chloride solution and then saturated sodium chloride solution, dried with anhydrous magnesium sulfate, and concentrated under reduced pressure to give crude ethyl 2-chloro-4-(1-pyrazolyl)methylphenoxyacetate as an oil.

To an anhydrous tetrahydrofuran (100 ml) suspension of 1.2 g of lithium aluminum hydride was added dropwise a solution of the above crude ethyl 2-chloro-4-(1-pyrazolyl)methylphenoxyacetate dissolved in 20 ml of anhydrous tetrahydrofuran at −78° C. under stirring over 30 minutes. The mixture was stirred at the same temperature for 1 hour and at −20° C. for further 2 hours. The reaction mixture was cooled again to −78° C., to which 1.2 ml of water, 1.2 ml of 15% aqueous sodium hydroxide solution and then 3.6 ml of water were added dropwise at the same temperature and subsequently 100 ml of toluene, 100 ml of tetrahydrofuran and then 50 g of anhydrous sodium sulfate were added, and the mixture was stirred at room temperature for 2 hours. The reaction mixture was filtered through celite, and the filtrate was concentrated under reduced pressure. The residue was subjected to silica gel column chromatography, which afforded 4.48 g of 2-[2-chloro-4-(pyrazolyl)methylphenoxy]ethanol as white crystals. Yield, 74% (based upon 2-chloro-4-(1-pyrazolyl)methylphenol).

m.p., 88.7° C.

Reference Production Example 4

Production of 2-chloro-4-(2-2H-1,2,3-triazolyl)methylphenol (1) Production of 2-chloro-4-(2-2H-1,2,3-triazolyl)methylphenyl 2,2-dimethylpropanoate A mixture of 2.26 g of 2H-1,2,3-triazole, 1.31 g of sodium hydride (60% oil dispersion) and 100 ml of anhydrous N,N-dimethylformamide was stirred at 60° to 70° C. under a nitrogen atmosphere for 2 hours. After the evolution of hydrogen gas ceased, the mixture was cooled to 10° C. To this mixture was added dropwise an anhydrous N,N-dimethylformamide (150 ml) solution of 10 g of 4-bromomethyl-2-chlorophenyl 2,2-dimethylpropanoate at room temperature under stirring over 1 hour, and the mixture was stirred at 80° C. for 1 hour. After cooling, the reaction mixture was poured into ice water, which was extracted with ethyl acetate. The organic layer was washed with saturated aqueous ammonium chloride solution and then saturated sodium chloride solution, dried with anhydrous magnesium sulfate, and concentrated under reduced pressure. The residue was subjected to silica gel column chromatography, which afforded 2-chloro-4-(2-2H-1,2,3-triazolyl) methylphenyl 2,2-dimethylpropanoate.

(2) Production of 2-chloro-4-(2-2H- 1 ,2,3-triazolyl) methylphenol

A mixture of 3 g of 2-chloro-4-(2-2H-1,2,3-triazolyl) methylphenyl 2,2-dimethylpropanoate, 10 ml of 20% aqueous sodium hydroxide solution and 60 ml of ethanol was heated at reflux for 5 hours. The reaction mixture was then concentrated under reduced pressure, to which water was added, and the mixture was adjusted to pH 6.0 with concentrated hydrochloric acid. This mixture was extracted with ethyl acetate. The organic layer was washed with water, dried with anhydrous magnesium sulfate, and concentrated under reduced pressure. The residue was subjected to silica gel column chromatography, which afforded 2-chloro-4-(2-2H-1,2,3-triazolylmethyl)phenol.

Reference Production Example 5

Production of 2-chloro-4-(2-pyridon-1-yl)methylphenol (1) Production of 2-chloro-4-(2-pyridon-1-yl) methylphenyl 2,2-dimethylpropanoate A mixture of 3.11 g of 2-pyridone, 1.31 g of sodium hydride (60% oil dispersion) and 100 ml of anhydrous N,N-dimethylformamide was stirred at 60° to 70° C. under a nitrogen atmosphere for 2 hours. After the evolution of hydrogen gas ceased, the mixture was cooled to 10° C. To this mixture was added dropwise an anhydrous N,N-dimethylformamide (150 ml) solution of 10 g of 4-bromomethyl-2-chlorophenyl 2,2-dimethylpropanoate at room temperature under stirring over 1 hour, and the mixture was stirred at 80° C. for 1 hour. After cooling, the mixture was poured into ice water, which was extracted with ethyl acetate. The organic layer was washed with saturated aqueous ammonium chloride solution and then saturated sodium chloride solution, dried with anhydrous magnesium sulfate, and concentrated under reduced pressure. The residue was subjected to silica gel column chromatography, which afforded 7.60 g of 2-chloro4-(2-pyridon-1-yl)methylphenyl 2,2-dimethylpropanoate as white crystals. Yield, 73%.

m.p., 145.2° C.

(2) Production of 2-chloro-4-(2-pyridon-1-yl) methylphenol

A mixture of 7.6 g of 2-chloro-4-(2-pyridon-1-yl) methylphenyl 2,2-dimethylpropanoate, 19 ml of 20% aqueous sodium hydroxide solution and 200 ml of ethanol was heated at reflux for 5 hours. The reaction mixture was then concentrated under reduced pressure, to which water was added, and the mixture was adjusted to pH 6.0 with concentrated hydrochloric acid. This mixture was extracted with ethyl acetate. The organic layer was washed with water, dried with anhydrous magnesium sulfate, and concentrated under reduced pressure. The residue was subjected to silica gel column chromatography, which afforded 3.98 g of 2-chloro-4-(2-pyridon-1-yl)methylphenol as white crystals. Yield, 71%.

m.p., 193.5° C.

Reference Production Example 6

Production of 2-[4-(1-pyrazolyl)methylphenoxy]ethyl bromide

To a mixture of 15 g of 4-(1-pyrazolyl)methylphenol, 32.4 g of 1,2-dibromoethane and 150 ml of water was added dropwise 30 ml of an aqueous solution of 4.1 g of sodium hydroxide while stirring under heating at reflux over 2 hours. Then, after heating at reflux under stirring for further 30 minutes, the reaction mixture was poured into 200 ml of ice water, which was extracted twice with 100 ml of diethyl ether. The organic layers were combined, washed with 5N aqueous sodium hydroxide solution, water and then saturated sodium chloride solution, dried with anhydrous magnesium sulfate, and concentrated under reduced pressure. The residue was subjected to silica gel column chromatography, which afforded 11.44 g of 2-[4-(1-pyrazolyl)methylphenoxy]ethyl bromide as white crystals. Yield, 47%.

m.p. 63–65° C.

The following will describe formulation examples for the harmful-organism controlling agents containing the present compounds as the active ingredients, in which "parts" are by weight and the present compounds are designated by their compound numbers as shown in Table 3.

Formulation Example 1 Emulsifiable concentrates

Ten parts of each of the present compounds 1 to 10 is dissolved in 35 parts of xylene and 35 parts of dimethylformamide, to which 14 parts of polyoxyethylene styryl phenyl ether and 6 parts of calcium dodecylbenzenesulfonate are added, and the mixture is well stirred to give a 10% emulsifiable concentrate of each compound.

Formulation Example 2 Wettable powders

Twenty parts of each of the present compounds 1 to 10 is added to a mixture of 4 parts of sodium lauryl sulfate, 2 parts of calcium lignin sulfonate, 20 parts of synthetic hydrated silicon oxide fine powder and 54 parts of diatomaceous earth, and the mixture is stirred with a juice mixer to give a 20% wettable powder of each compound.

Formulation Example 3 Granules

To 5 parts of each of the present compounds 1 to 10 are added 5 parts of synthetic hydrated silicon oxide fine powder, 5 parts of sodium dodecylbenzenesulfonate, 30 parts of bentonite and 55 parts of clay, and the mixture is well stir-red. A suitable amount of water is then added to this mixture, which is further stirred, granulated with a granulator, and air-dried to give a 5% granule of each compound.

Formulation Example 4 Dusts

To 2 parts of each of the present compounds 1 to 10 is added 5 parts of polypropylene glycol, and the mixture is heated over the melting point for dissolution, which is then absorbed in 93 parts of granular calcined diatomaceous earth, which has been warmed, to give a 2% granule of each compound.

Formulation Example 5 Dusts

One part of each of the present compounds 1 to 10 is dissolved in a suitable amount of acetone, to which 5 parts of synthetic hydrated silicon oxide fine powder, 0.3 part of PAP and 93.7 parts of clay are added, and the mixture is stirred with a juice mixer. The removal of acetone by evaporation gives a 1% dust of each compound.

Formulation Example 6 Water-based suspension

Twenty parts of each of the present compounds 1 to 10 and 1.5 parts of sorbitan trioleate are mixed with 28.5 parts of an aqueous solution containing 2 parts of polyvinyl alcohol, and the mixture is pulverized into fine particles (particle size, not more than 3 μm) with a sand grinder, to which 40 parts of an aqueous solution containing 0.05 part of xanthane gum and 0.1 part of aluminum magnesium silicate is added and then 10 parts of propylene glycol is added. The mixture is stirred to give a 20% water-based suspension of each compound.

Formulation Example 7 Oil sprays

First, 0.1 part of each of the present compounds 1 to 10 is dissolved in 5 parts of xylene and 5 parts of trichloroethane. The solution is then mixed with 89.9 parts of deodorized kerosine to give a 0.1% oil spray of each compound.

Formulation Example 8 Oil-based aerosols

First, 0.1 part of each of the present compounds 1 to 10, 0.2 part of tetramethrin, 0.1 part of d-phenothrin, 10 parts of trichloroethane and 59.6 parts of deodorized kerosine are mixed for dissolution. The solution is put in an aerosol vessel, which is then equipped with a valve. Through the said valve, 30 parts of a propellant (liquefied petroleum gas) is charged under increased pressure to give an oil-based aerosol of each compound.

Formulation Example 9 Water-based aerosols

First, 0.2 part of each of the present compounds 1 to 10, 0.2 part of d-allethrin, 0.2 part of d-phenothrin, 5 parts of xylene, 3.4 parts of deodorized kerosine and 1 part of an emulsifier [ATMOS 300 (registered trade name by Atlas Chemical Co.)] are mixed for dissolution. The mixture, together with 50 parts of pure water, is put in an aerosol vessel, which is then equipped with a valve. Through the said valve, 40 parts of a propellant (liquefied petroleum gas) is charged under increased pressure to give a water-based aerosol of each compound.

Formulation Example 10 Mosquito-coils

To 0.3 g of each of the present compounds 1 to 10 is added 0.3 g of d-allethrin, and the mixture is dissolved in 20 ml of acetone. The solution is uniformly mixed with 99.4 g of a carrier for mosquito-coils (prepared by mixing Tabu powder, pyrethrum marc powder and wood flour at the ratio of 4:3:3) under stirring, to which 120 ml of water was added. The mixture is well kneaded, molded, and dried to give a mosquito-coil of each compound.

Formulation Example 11 Electric mosquito-mats

To 0.4 g of each of the present compounds 1 to 10, 0.4 g of d-allethin and 0.4 g of pipenyl butoxide is added acetone for dissolution, so that the total volume comes to 10 ml. This solution in 0.5 ml is uniformly absorbed in a substrate forelectric mosquito-mats (prepared by pressing a fibrillated mixture of cotton linter and pulp into a sheet), which is 2.5 cm×1.5 cm and 0.3 cm thick, to give an electric mosquito-mat of each compound.

Formulation Example 12 Heating smoke formulations

First, 100 mg of each of the present compounds 1 to 10 is dissolved in a suitable amount of acetone, and the solution is then absorbed in a porous ceramic plate of 4.0 cm×4.0 cm and 1.2 cm thick to give a heating fumigant of each compound.

Formulation Example 13 Poison baits

First, 10 mg of each of the present compounds 1 to 10 is dissolved in 0.5 ml of acetone, and this solution is added to 5 g of solid bait powder for animals (Breeding Solid Feed Powder CE-2, trade name by Japan Clea Co., Ltd.), which is uniformly mixed. Then, the removal of acetone by air drying gives a 0.5% poison bait of each compound.

The following test examples will demonstrate that the present compounds are useful as the active ingredients of harmful-organism controlling agents, in which the present compounds are designated by their compound numbers as shown in Table 3.

Test Example 1 Insecticidal test against common mosquito

An emulsifiable concentrate of the test compound obtained according to Formulation Example 1 was diluted with water, and this dilution in 0.7 ml was added to 100 ml of ion-exchanged water to a prescribed concentration. Twenty last instar larvae of common mosquito (*Culex pipiens pallens*) were set free therein, and bred while giving bait for 8 days. The emergence inhibitory rate was determined by the following equation 1. The results are shown in Table 4.

$$\text{Emergence inhibitory rate (\%)} = \frac{\text{Emergence rate in untreated group} - \text{Emergence rate in treated group}}{\text{Emergence rate in untreated group}} \times 100 \quad [1]$$

TABLE 4

| Test compound | Application concentration (ppm) | Emergence inhibitory rate (%) |
| --- | --- | --- |
| 1 | 3.5 | 100 |
| 1 | 0.1 | 100 |
| 2 | 3.5 | 100 |
| 3 | 3.5 | 100 |
| 4 | 3.5 | 100 |
| 4 | 0.1 | 100 |

Test Example 2 Insecticidal test against cotton aphid

An emulsifiable concentrate of the test compound obtained according to Formulation Example 1 was diluted with water to a prescribed concentration, and the dilution was poured upon the parts near the roots of cucumbers cultivated in polyethylene cups for flooding at a rate of 10 cc/1 pot. After 3 days from the treatment, five adults of cotton aphid (*Asphis gossypii*) were freely bred on the main leaves. After 14 days from the free breeding, the control value was determined by the following equation 2. The results are shown in Table 5.

$$\text{Control value (\%)} = \left(1 - \frac{C_b \cdot T_{ai}}{T_b \cdot C_{ai}}\right) \times 100 \quad [2]$$

where $C_b$ is the number of insects before the treatment in the untreated group; $C_{ai}$, the number of insects during the observation in the untreated group; $T_b$, the number of insects before the treatment in the experimental group; and $T_{ai}$, the number of insects during the observation the experimental group.

TABLE 5

| Test compound | Application concentration (ppm) | Control value (%) |
| --- | --- | --- |
| 1 | 500 | 82 |
| 2 | 500 | 96 |
| 5 | 500 | 100 |
| 6 | 500 | 90 |
| 8 | 500 | 79 |

Industrial Applicability

According to the present invention, there are provided novel ether compounds having excellent controlling effects against harmful organisms. These ether compounds are useful as the active ingredients of harmful-organism controlling agents.

We claim:

1. An ether compound of the formula:

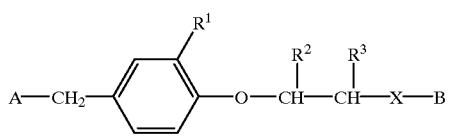
(P-1)

wherein $R^1$ is hydrogen or chlorine;

$R^2$ and $R^3$ are independently hydrogen or methyl;

A is a group of the formula:

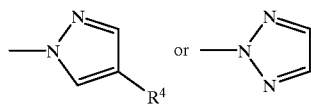

wherein $R^4$ is hydrogen, chlorine or methyl;

B is a group of the formula:

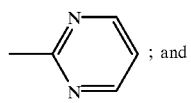
; and

X is oxygen or sulfur.

2. An ether compound according to claim 1, wherein A is a group of the formula:

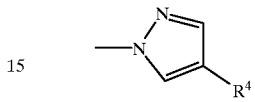
(P-2)

wherein $R^4$ is as defined above.

3. An ether compound according to claim 2, wherein $R^4$ is hydrogen.

4. An ether compound according to claim 1, wherein $R^1$ is hydrogen.

5. 4-(1-Pyrazolyl)methylphenyl 2-(2-pyrimidyloxy) ethyl ether.

6. An insecticidal and/or acaricidal agent comprising an effective amount of an ether compound according to claim 1 as an active ingredient, and a carrier.

* * * * *

UNITED STATES PATENT AND TRADEMARK OFFICE
CERTIFICATE OF CORRECTION

PATENT NO : 5,972,949
DATED : October 26, 1999
INVENTOR(S): SHUTO et al.

It is certified that error appears in the above-identified patent and that said Letters Patent is hereby corrected as shown below:

On the title page:

In the Related U.S. Application Data at item [62] adding as a second sentence --Application No. 08/727,565 is the national phase of the PCT International Application No. PCT/JP95/00763 filed on April 19, 1995 under 35 U.S.C. 371.--

Signed and Sealed this

Twelfth Day of December, 2000

Attest:

Q. TODD DICKINSON

Attesting Officer

Director of Patents and Trademarks